(12) United States Patent
Nishida et al.

(10) Patent No.: US 6,387,497 B1
(45) Date of Patent: May 14, 2002

(54) SYNTHETIC ORGANIC PARTICLES, PROCESS FOR THE PRODUCTION OF THE SAME, AND USE THEREOF

(75) Inventors: Mitsutoshi Nishida; Ichiro Takahara, both of Yao (JP)

(73) Assignee: Matsumoto Yushi-Seiyaku Co Ltd, Osaka (JP)

( * ) Notice: Subject to any disclaimer, the term of this patent is extended or adjusted under 35 U.S.C. 154(b) by 0 days.

(21) Appl. No.: 09/485,418

(22) PCT Filed: Dec. 17, 1998

(86) PCT No.: PCT/JP98/05719

§ 371 Date: Feb. 10, 2000

§ 102(e) Date: Feb. 10, 2000

(87) PCT Pub. No.: WO99/32533

PCT Pub. Date: Jul. 1, 1999

(30) Foreign Application Priority Data

Dec. 19, 1997 (JP) ................................................ 9-365147

(51) Int. Cl.⁷ ................................................ B32B 5/16
(52) U.S. Cl. ...................... 428/403; 428/407; 525/309; 525/310; 523/201; 523/202
(58) Field of Search ................................ 428/407, 403; 525/309, 310; 523/201, 202

(56) References Cited

U.S. PATENT DOCUMENTS 5,183,859 A * 2/1993 Sasaki
6,027,806 A * 2/2000 Abe ........................... 428/407
6,172,135 B1 * 1/2001 Fraser ........................ 523/201
6,180,694 B1 * 1/2001 Bugnon ...................... 523/205

FOREIGN PATENT DOCUMENTS

| JP | 62198612 | 9/1987 |
| JP | 6251931 | 11/1987 |
| JP | 2225510 | 9/1990 |
| JP | 337210 | 2/1991 |
| JP | 7291845 | 11/1995 |
| JP | 7316242 | 12/1995 |
| JP | 93134 | 1/1997 |
| JP | 911086 | 4/1997 |
| JP | 9118726 | 5/1997 |
| JP | 9194542 | 7/1997 |

* cited by examiner

Primary Examiner—Leszek Kiliman

(57) ABSTRACT

Synthetic organic particles each constituted of a core made from an organic polymer and a surface layer formed from a methacrylate resin on the surface of the core. In one of the particles, the core is made from a copolymer comprising 80 to 99 weight percent of a lower alkyl acrylate and 1 to 20 weight percent of a polyfunctional vinyl monomer to exhibit rubberlike elasticity, while in another of the particles, the core is made from a copolymer of a reactive benzotriazol compound and a (meth)acrylic monomer to exhibit an ultraviolet absorbing activity. These synthetic organic particles can be suitably added to cosmetics to impart a feeling of creamy softness and an ultraviolet screening power to them.

29 Claims, No Drawings

SYNTHETIC ORGANIC PARTICLES, PROCESS FOR THE PRODUCTION OF THE SAME, AND USE THEREOF

TECHNICAL FIELD

The present invention relates to synthetic organic particles, a process for producing the same, and the use thereof. More precisely, the present invention relates to synthetic organic particles having elasticity like rubber or ultraviolet ray absorbing function, a process for producing the same, and their application to cosmetics.

PRIOR ART

Various powders have been used as cosmetic powder materials. They include various inorganic powders, for example, natural minerals such as talc, sericite, and muscovite; and metal oxides such as titanium oxide, lead oxide, and zinc oxide.

On the other hand, finely powdered products of natural organic materials such as cellulose or silk have also been used. Recently, various materials, such as finely powdered synthetic resins, or fine particles synthesized in a special process have been frequently applied to cosmetics. The examples of such materials are nylon powder, polyacrylonitrile powder, polyester powder, polystyrene powder, polypropylene powder, polyethylene powder, tetrafluoroethylene powder, polymethylmethacrylate powder, silicone powder, and the like.

These powders synthesized from organic polymers can be more easily processed into uniform particle sizes and shapes in their synthesizing processes than inorganic powders. In addition, they possess other advantages, such as low oppression on skin owing to their low specific gravity. Hence they have been recently consumed in great quantity.

The powders of natural minerals or metal oxides are not proper as the powder material for cosmetics. Because their particle shape isn't uniform, varying into sphere, scale, needle, and amorphous shapes, and their particle size also varies from several to several dozens of microns. In addition, inorganic compounds are not compatible to skin due to their high specific gravity, and cause some troubles such as rough touch on skin.

Organic fine particles used as powder materials for cosmetics are usually made of all-purpose resins. And the powders of oval or spherical particle shape are preferred because the powders of scale or needle-like particle shape or amorphous shape obtained by mechanical pulverization give rough touch on skin. Particularly, spherical fine particles give better smoothness on skin than others owing to its rolling effect.

The development of spherical fine particles having rubbery elasticity for cosmetics has been required because most of organic fine particles don't give satisfactory soft touch to skin due to their poor elasticity. A process for producing elastic acrylic fine particles is disclosed in Japanese Patent Laid-Open Application 3-37201. The particles disclosed therein can exist in the shape of spherical particles only in a dispersion medium, and fuse to coagulate into lumps through drying process. Such coagulated particles cannot be separated into powder.

By the way, cosmetics containing an ultraviolet-ray absorber are used to screen or absorb ultraviolet ray, the ray which is contained in the sunlight and causes sunburn, liver spots, or freckles on human skin.

The ultraviolet-ray absorbers currently used include inorganic pigments, which screen ultraviolet ray, such as titanium dioxide, zinc oxide, and iron oxide; and organic ultraviolet-ray absorbers, which absorb ultraviolet ray. The above inorganic pigments cover skin for screening ultraviolet ray, and they cannot be blended a lot in cosmetics, because they whiten or color skin.

On the contrary, organic ultraviolet-ray absorbers absorb ultraviolet ray without covering skin, and do not cause such problems as whitening or coloring of skin. This is the reason why organic ultraviolet-ray absorbers have been increasingly used as the ultraviolet-ray absorbers for cosmetics in recent years.

However, many of the organic ultraviolet-ray absorbers irritate skin due to their skin-irritation property when they are directly blended with other cosmetic materials and applied to skin.

For preventing such organic ultraviolet-ray absorbers from direct contact to skin, it has been proposed to disperse and confine them in the inside of resin particles. Japanese Patent Publication 62-51931 and Japanese Patent Laid-Open Application 62-198612 disclose resin particles in which such organic ultraviolet-ray absorbers are encapsulated.

The encapsulation of organic ultraviolet-ray absorbers in resin particles was supposed to minimize the direct contact of ultraviolet-ray absorbers to skin, and to achieve lower skin irritation than that by cosmetics to which ultraviolet-ray absorbers were directly blended. Consequently, the use of resin particles in which organic ultraviolet-ray absorbers were encapsulated was expected to eliminate skin irritation. But actually skin irritation by ultraviolet-ray absorbers sometimes occurred even with such resin particles.

Because the organic ultraviolet-ray absorbers were only physically encapsulated in the pores of the resin particles, not being combined to the molecules of the resin, and were carried out of the pores by the base oils of cosmetics when such base oils penetrate into the pores. In an actual measurement, the amount of organic ultraviolet-ray absorbers, which were carried out of resin particles sometimes, reached to several percent of the whole of the absorbers encapsulated in resin particles. The ultraviolet-ray absorbers carried out of resin particles have caused skin irritation.

Japanese Patent Laid-Open Application 7-291845 discloses resin particles, which release slight ultraviolet-ray absorbers. However, even such resin particles irritate skin due to the direct contact of benzotriazole skeleton, which has ultraviolet-ray absorbing function and is combined with the molecules of the resin.

DISCLOSURE OF INVENTION

The object of the present invention is to provide synthetic organic particles having rubbery elasticity or ultraviolet-ray absorbing function.

Another object of the present invention is to provide, synthetic organic particles having sufficient rubbery elasticity and shape-retaining property.

Further object of the present invention is to provide synthetic organic particles having rubbery elasticity, which are blended in cosmetics to attain rolling effect, spreadability and dry or soft creamy touch on skin.

Further object of the present invention is to provide synthetic organic particles possessing sufficient ultraviolet-ray absorbing function and shape-retaining property.

Further object of the present invention is to provide synthetic organic particles, which are blended in cosmetics to impart sufficient ultraviolet-ray absorbing property to the cosmetics without irritating skin.

Further object of the present invention is to provide an industrially advantageous process for producing the said synthetic organic particles.

Further object of the present invention is to provide cosmetics containing the said synthetic organic particles as the application thereof.

Further objects and advantages of the present invention will be apparent from the following description.

The above objects and advantages of the present invention are achieved, first, with synthetic organic particles (hereinafter referred to as the first synthetic organic particles of the present invention) characterized by comprising:

(A) cores of an organic polymer, the organic polymer being a copolymer comprising 80 to 99 weight percent of a lower alkyl acrylate and 1 to 20 weight percent of a polyfunctional vinyl monomer, and having rubbery elasticity, and (B) a surface layer of a methacrylate resin formed on the surface of the said cores; and having (C) rubbery elasticity.

Second, the above objects and advantages of the present invention are achieved with synthetic organic particles (hereinafter referred to as the second synthetic organic particles of the present invention) characterized by comprising:

(A') cores of an organic polymer, the organic polymer being a copolymer of a reactive benzotriazole compound and a (meth)acrylic monomer, and having ultraviolet-ray absorbing function, and (B') a surface layer of a methacrylate resin formed on the surface of the said cores; and having (C') ultraviolet-ray absorbing function.

At first, the first synthetic organic particles of the present invention are explained as follows.

Each of the first synthetic organic particles of the present invention comprises with a core and a surface layer formed on the surface of the core.

The cores comprise a copolymer of lower alkyl acrylates and a polyfunctional vinyl monomer. The preferable lower alkyl acrylates to be used for the cores are acrylates esterified with alkyl groups having 1 to 4 carbon atoms. The examples of such acrylates are methyl acrylate, ethyl acrylate, n-butyl acrylate, and i-butyl acrylate. Acrylates having small number of carbon atoms are preferable for producing resilient particles while acrylates having large number of carbon atoms are preferable for producing soft particles. Two or more of those acrylates can be combined to produce cores.

The polyfunctional vinyl monomers used for the cores are those having at least two ethylenically unsaturated bonds in a molecule, for example, aromatic cross-linking agents, such as divinyl benzene, or acrylic cross-linking agents, such as (poly)ethyleneglycol di(meth)acrylate and trimethylolpropane tri(meth)acrylate. Acrylic cross-linking agents are preferable because of their weathering resistance.

The composition of the monomers forming the cores comprises 80 to 99 weight percent of the said lower alkyl acrylate and 1 to 20 weight percent of the said polyfunctional vinyl monomer. Less than 1 weight percent of the polyfunctional vinyl monomer in the composition is inefficient for maintaining the shape of the cores in their production process, and more than 20 weight percent of the vinyl monomer produces final particles of poor softness, which cannot attain soft touch on skin. The preferable amount of the polyfunctional vinyl monomer is 3 to 15 weight percent.

The cores are spherical resin particles having an average diameter of 1 to 16 $\mu$m, preferably 3 to 13 $\mu$m.

The first synthetic organic particles of the present invention have a surface layer of methacrylate resin formed on the surface of the above-mentioned cores.

The surface layer is preferably formed of a polymer of lower alkyl methacrylates, or a copolymer of lower alkyl methacrylates and a polyfunctional vinyl monomer.

The preferable lower alkyl methacrylates used for the surface layer are methacrylates esterified with an alkyl group of 1 to 4 carbon atoms such as, methyl methacrylate, ethyl methacrylate, n-butyl methacrylate, or i-butyl methacrylate. Two or more of the methacrylates can be used in combination.

The polyfunctional vinyl monomers used for the surface layer are the same as the monomers used for the said cores.

The average thickness of the surface layer is usually 0.01 to 1 $\mu$m, and preferably 0.05 to 0.5 $\mu$m. The surface layer thinner than the said range often causes deformation or fusing of particles in their production process, and that thicker than the said range cannot produce particles of rubbery elasticity.

The average diameter of the first synthetic organic particles of the present invention having the above layer ranges usually from 1.02 to 18 $\mu$m, preferably from 3.1 to 14 $\mu$m.

The first synthetic organic particles of the present invention can preferably be produced in the following process.

A process for producing synthetic organic particles (hereinafter referred to as the first process of the present invention) is characterized by the following steps comprising:

(1) copolymerizing 80 to 99 weight percent of lower alkyl acrylates and 1 to 20 weight percent of a polyfunctional vinyl monomer in an aqueous medium to form core particles of an organic polymer having rubbery elasticity, and (2) adding a lower alkyl methacrylate or adding a lower alkyl methacrylate and a polyfunctional vinyl monomer in the polymerization system containing the said core particles, and polymerizing the added monomers on the surface of the said core particles to form a layer of a methacrylate resin on the surface of the said core particles.

The lower alkyl acrylates and polyfunctional vinyl monomers used in the step (1) of the first process of the present invention are the same as exemplified above.

Water is usually employed as the aqueous medium in the process. And water-soluble organic solvents, such as alcohols, may be blended in the aqueous medium.

Emulsifiers and dispersion stabilizers can be applied for dispersing the above monomers in the aqueous medium. And the cores formed in the step (1) can be produced through emulsion polymerization, soap-free emulsion polymerization, suspension polymerization, or seed polymerization. The examples of the emulsifiers used for emulsion polymerization are alkylbenzene sulfonate, such as sodium dodecylbenzene sulfonate; polyethylene glycol alkylether, such as polyethylene glycol nonyphenyl ether; and reactive emulsifiers having reactive groups, such as vinyl, acryloyl, or allyl groups. The examples of dispersion stabilizers are water-soluble polymers, such as polyvinyl alcohols or polyacrylates. The amount of those emulsifiers and dispersion stabilizers are 0.1 to 5 parts by weight of 1 00 parts by weight of the monomers.

The monomers used for producing the cores are dispersed in an aqueous medium with dispersing device, such as homogenizers. The reaction initiators applicable at this stage are azo compounds, such as azobisisobutyronitrile; organic peroxides, such as benzoyl peroxide, and lauroyl peroxide;

and persulfates, such as potassium persulfate, and ammonium persulfate. The amount of such reaction initiators is 0.1 to 5 parts by weight to 100 parts by weight of the monomers.

Purging the reaction vessels with an inert gas, such as nitrogen, is preferable for polymerizing the monomers dispersed in an aqueous medium as described above. After purging the reaction vessels with an inert gas, polymerization reaction is carried out by heating the reactive liquid up to 60 to 80° C.

The time required for producing the polymer particles for forming the cores is usually 5 to 8 hours under the above reactive condition.

In the first process of the present invention, monomers are added in the aqueous medium in the step (2) to form a layer on the surface of the core particles of the polymer, which are produced in the step (1) as described above. In other words, the monomers added in the aqueous medium polymerize to cover the surface of the core particles produced in the step (1), and form surface layer.

The monomers added in the step (2) are lower alkyl acrylates or the combination of a lower alkyl acrylate and a polyfunctional vinyl monomer. The examples of the lower alkyl acrylates and polyfunctional vinyl monomer are the same as those mentioned above.

The step (2) is carried out specifically in the following manner. Monomers are added in the aqueous medium containing the core particles and the aqueous medium is agitated with an agitator. The preferable amount of the monomers is 5 to 30 weight percent of the monomers used for forming the core particles. Usually, it is preferably to add reaction initiators in the aqueous medium.

A part of the monomers added as described above adhere onto the surface of the core particles produced in the step (1). After adding the monomer, the monomers on the surface of the core particles are polymerized to form a surface layer of methacrylate resin through heating the reactive liquid up to 60 to 80° C. The time required for forming the surface layer is usually 3 to 6 hours.

After forming the surface layer as mentioned above, the resultant particles are separated out through filtration and centrifugal separation, and washed to remove emulsifiers, dispersion stabilizers, and remaining monomers. The particles are processed into the acrylic synthetic organic particles having rubbery elasticity of the present invention through drying and pulverizing process.

The following description explains the second synthetic organic particles of the present invention.

The second synthetic organic particles of the present invention are defined by following (A'), (B') and (C').

The second synthetic organic particles of the present invention comprise:

(A') cores of organic polymer, the said organic polymer being a copolymer of a reactive benzotriazol compound and a (meth)acrylic monomer, and having ultraviolet-ray absorbing function; and (B') a surface layer of methacrylate resin formed on the surface of the above cores; and having (C') ultraviolet-ray absorbing function.

The preferable reactive benzotriazole compound of the present invention is a compound represented by the following formula (1).

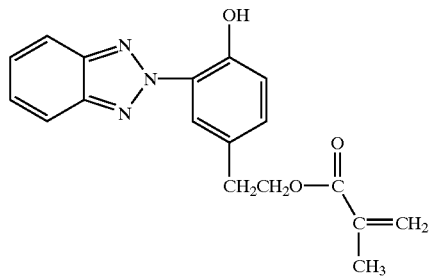

The compound has ultraviolet-ray absorbing function owing to the benzotriazole structure, and is polymerizable owing to the methacryloyl and acryloxy groups. Thus the compound has both superior ultraviolet-ray absorbing function and high reactivity with acrylic compounds.

The examples of the (meth)acrylic monomer are methyl (meth)acrylate, ethyl (meth)acrylate, propyl (meth)acrylate, butyl (meth)acrylate, 2-ethylhexyl (meth)acrylate, lauryl (meth)acrylate, stearyl (meth)acrylate, cyclohexyl (meth) acrylate, 2-hydroxyethyl (meth)acrylate, 2-propyl (meth) acrylate, chloro-2-hydroxyethyl (meth)acrylate, diethyleneglycol mono(meth)acrylate, methoxyethyl (meth) acrylate, glycidyl (meth)acrylate, dicyclopentanyl (meth) acrylate, dicyclopentenyl (meth)acrylate, and isobornyl (meth)acrylate.

The preferable organic polymer is one of the copolymers containing polyfunctional monomers having two or more functional groups in each of their copolymer chain in addition to the said reactive benzotriazole compound and (meth)acrylic monomers. The examples of such polyfunctional monomers are ethyleneglycol di(meth)acrylate, triethyleneglycol (meth)acrylate, tetraethyleneglycol (meth) acrylate, trimethylolpropane tri(meth)acrylate, pentaerythritol tri(meth)acrylate, 1,1,1-trihydroxy methylethane triacrylate, 1,1,1-trishydroxymethyl methylethane triacrylate, 1,1,1-trishydroxymethylpropane triacrylate, and vinyl benzene.

The preferable amount of the reactive benzotriazole compound being combined in the said organic polymer is 1 to 40 parts by weight, more preferably 10 to 30 parts by weight to 100 parts by weight of (meth)acrylic monomers.

The preferable amount of the polyfunctional monomers being combined in the said organic polymer is 0.5 to 60 weight percent of the whole of the monomers constituting the said organic polymer.

The cores are spherical resin particles, of which average diameter is usually 1 to 16 μm, preferably 3 to 13 μm.

The second synthetic organic particles of the present invention have a surface layer of methacrylate resin on the surface of their cores mentioned above.

Preferable materials for the surface layer are the polymers of lower alkyl methacrylates, or the copolymers of lower alkyl methacrylates and polyfunctional vinyl monomers. The lower alkyl methacrylates for polymerizing the said polymers or copolymers are methacrylates esterified with alkyl groups of 1 to 4 carbon atoms, such as methyl methacrylate, ethyl methacrylate, n-butylmethacrylate, and i-butyl methacrylate. The combination of two or more of those acrylates can also be used for the said polymer. The polyfunctional vinyl monomers for forming the surface layer are those having two or more ethylenically unsaturated bonds in their molecules. Those are aromatic cross-linking agents, such as divinyl benzene, or acrylic cross-linking agents, such as (poly)ethyleneglycol di(meth)acrylate, and trimethylolpropane tri(meth)acrylate. Among those, the acrylic cross-linking agents are preferable from an aspect of weatherability.

The average thickness of the surface layer is usually 6.01 to 1 μm, and preferably 0.05 to 0.5 μm. Thinner layers beyond the above range cannot prevent the migration of unreacted portion of reactive benzotriazole compounds from the cores in some cases. And thicker layers beyond the above range-often inhibit the production of particles.

The average diameter of the second synthetic organic particles of the present invention, having the above-mentioned surface layer, is usually 1.02 to 18 μm, and preferably 3.1 to 14 μm.

The second synthetic organic particles of the present invention are preferably produced in the following process (hereinafter referred to as the second process of the present invention) characterized by the steps comprising:

(1) dispersing a reactive benzotriazole compound, a (meth)acrylic monomer, and toluene in an aqueous medium, and polymerizing the compound and monomer to produce polymer particles in which toluene is encapsulated;

(2) adding lower alkyl methacrylates, or a combination of a lower alkyl methacrylate and a polyfunctional vinyl monomer in the polymerization system containing the said polymer particles, and polymerizing the added monomers on the surface of the said polymer particles to form a layer of a methacrylate resin; and, (3) separating the polymer particles, having the surface layer and being produced in the step (2), and drying the particles to evaporate and remove the encapsulated toluene.

Water is usually employed as the aqueous medium in the step (1), and a water-soluble organic solvent, such as alcohols, can be added in the aqueous medium.

Toluene is also used in the step (1). Toluene contributes to minimizing the non-reacted part of a reactive benzotriazole compound. Because the crystallization of a reactive benzotriazole compound in step (1) can be minimized owing to the high solubility of the compound in toluene, when the reactive benzotriazole compound and the monomer for forming cores are dissolved uniformly in toluene and the solution is dispersed in the aqueous medium. The toluene encapsulated in the obtained polymer particles evaporates in the drying operation in the step (3), and doesn't remain in the particles of the present invention. However, excessive toluene in the polymerization system makes particles fragile due to increased pore area in cores after the evaporation of toluene, and insufficient toluene in the polymerization system is not effective to minimize the non-reacted part of reactive benzotriazole compounds. It is preferably to control the amount of toluene at a proper level, at which the polymer particles containing 10 to 70 weight percent of toluene in their pores are produced in the step (1).

The reactive benzotriazole compounds and (meth)acrylate monomers used in the step (1) are the same as those mentioned in the above examples. Polyfunctional monomers can also be used in the step (1). The examples of those polyfunctional monomers are the same as mentioned above. The preferable amount of the polyfunctional monomers is 0.5 to 60 weight percent of the whole of the monomers used for the cores. Insufficient amount of the polyfunctional monomers often causes swelling or melting of the polymer particles due to encapsulated toluene, and excessive amount of the polyfunctional monomers causes fragile polymer particles.

It is preferable to use emulsifiers or dispersion stabilizers for dispersing the above monomers and toluene in an aqueous medium. And the cores can be formed through emulsion polymerization, soap-free emulsion polymerization, suspension polymerization, or seed polymerization. The emulsifiers used for emulsion polymerization are alkylbenzene sulfonates, such as sodium dodecylbenzene sulfonate; polyethyleneglycol alkyl ethers, such as polyethyleneglycol nonylphenyl ether; and reactive emulsifiers having reactive groups, such as vinyl acryloyl or allyl groups. The examples of dispersion stabilizers are water-soluble polymers, such as polyvinyl alcohols or polyacrylates. The amount of the emulsifiers and dispersion stabilizers is usually 0.1 to 5 parts by weight to 100 parts by weight of the total of the monomers and toluene.

The monomers and toluene for producing the cores are usually dispersed in an aqueous medium with dispersing devices, such as homogenizers. The reaction initiators applicable to the step are azo compounds, such as azobisisobutyl nitryl; organic peroxides, such as benzoyl peroxide, or lauroyl peroxide; and persulfates such as potassium persulfate and ammonium persulfate. Those initiators are usually used in an amount of 0.1 to 5 parts by weight to 100 parts by weight of the monomers.

For polymerizing the monomers dispersed in an aqueous medium as mentioned above, it is preferable to purge a reaction vessel with inert gas, such as nitrogen. After purging a reaction vessel with inert gas, polymerization is carried out by heating the reaction liquid to 60 to 80° C.

The time required for producing the core polymer particles in which toluene is encapsulated is usually 5 to 8 hours under the above-mentioned condition.

In the second process of the present invention, the core polymer particles are produced in the step (1) as mentioned above, and monomers are added to the aqueous medium in the step (2) to form a surface layer on the surface of the polymer particles in which toluene is encapsulated. In other words, the surface layer is formed by polymerizing the monomers added in the aqueous medium to cover up the surface of the polymer particles (core) produced in the step (1), in which toluene is encapsulated.

Specifically, new monomers are added in the aqueous medium preferably in an amount of 5 to 30 weight percent of the total of the monomers and toluene used for forming the polymer particles, and agitated with an agitator. Usually a reaction initiator is also added to the aqueous medium.

Part of the monomers added to the aqueous medium adheres to the surface of the polymer particles produced in the above step. After adding the monomers, the monomers adhering on the surface of polymer particles are polymerized into surface layer through heating up the reaction liquid to 60 to 80° C. The reaction time for forming the surface layer is usually 3 to 6 hours.

After the surface layer is formed as described above the resultant particles are separated out from the system through filtration and centrifugal separation in the step (3). The separated particles are washed to remove the emulsifiers, dispersion stabilizers, and remained monomers, if necessary, and the particles are then dried to evaporate and remove the encapsulated toluene. Then the second synthetic organic particles of the present invention are produced through pulverization, if necessary.

The first and second synthetic organic particles of the present invention can be used as cosmetic particles.

And the present invention also provides cosmetics containing the above-mentioned synthetic organic particles.

The first synthetic organic particles of the present invention impart rolling effect, spreadability, and dry touch to cosmetics as well as the conventional synthetic hard polymer powder. In addition, the particles of the present invention can impart creamy soft touch to cosmetics, which couldn't have been attained by synthetic hard polymer powder. Thus the particles of the present invention are excellent as cosmetic powder materials.

The second synthetic organic particles of the present invention are formed with an ultraviolet-ray absorptive resin. And the migration of ultraviolet-ray absorbers from the particles of the resin produced with toluene is lower than that from the particles produced without toluene. In addition a methacrylate resin free of benzotriazol skeleton covers the surface of the particles of the ultraviolet-ray absorptive resin and prevents skin from direct contact to benzotriazol skeleton. Thus the cosmetics containing the second synthetic organic particles of the present invention do not result in the migration of ultraviolet-ray absorbers or rough skin due to the direct contact of ultraviolet-ray absorbers.

EXAMPLES

The present invention is explained in detail with the following examples, but shall not be restricted within the scope of those examples.

Example 1

An oil phase was prepared by mixing 135 g of ethyl acrylate, 15 g of ethyleneglycol dimethacrylate, and 1 g of azobisisobutylonitryl to obtain a homogeneous solution. And a water phase was prepared by adding and dissolving 1.6 g of methyl cellulose, 0.1 g of sodium dioctylsulfosuccinate, and 0.1 g of sodium hexamethaphosphate in 420 g of purified water.

Then the above oil phase and water phase were agitated at high speed with a T.K. Homomixer (produced by Tokushu Kika Kogyo K.K.) for 2 minutes to form a homogeneous suspension. Then the suspension was charged into a 1.5-liter autoclave. The inside atmosphere of the reaction system was replaced with $N_2$, and polymerization was carried out at 65° C. for 7 hours with agitation at 200 rpm. After 7 hours, the reacted liquid was cooled down to normal temperature.

The average diameter of the core polymer particles produced in the reaction was 9.0 $\mu$m. Then 20 g of methyl methacrylate containing 0.15 g of azobisisobutylonitryl, and 2.5 g of ethyleneglycol dimethacrylate were added to the reacted liquid, and the liquid was again heated to 65° C. to carry out the reaction for 5 hours with agitation at 200 rpm.

After the reaction, the reacted liquid was cooled down to normal temperature, and the produced particles and dispersion medium were separated by filtration. Then the particles were washed and filtered two times. The resultant particles were dried and pulverized into the powder of fine particles of the present invention. The average particle diameter of the powder was 9.4 $\mu$m and a layer of 0.2 $\mu$m average thickness was formed on the surface of the cores of the particles.

Example 2

The procedure was carried out in the same manner as in Example 1, except that 60 g of methyl acrylate, 80 g of butyl acrylate, and 10 g of ethyleneglycol dimethacrylate were used as the monomers for forming cores. And the powder of fine particles of the present invention having an average particle diameter of 9.4 $\mu$m, average core diameter of 9.0 $\mu$m, and average surface layer thickness of 0.2 $\mu$m, was obtained.

Example 3

The procedure was carried out in the same manner as in Example 1, except that 17.5 g of ethyl methacrylate, and 5 g of ethyleneglycol dimethacrylate were used as the monomers for forming a surface layer. And the powder of fine particles of the present invention having an average particle diameter of 8.5 $\mu$m, average core diameter of 8.2 $\mu$m, and average surface layer thickness of 0.15 $\mu$m, was obtained.

Comparative Example 1

The procedure was carried out in the same manner as in Example 1, except that 105 g of ethyl acrylate, and 45 g of ethyleneglycol dimethacrylate were used as the monomers for forming cores. And the powder of fine particles having an average particle diameter of 8.0 $\mu$m average core diameter of 7.6 $\mu$m, and average surface layer thickness of 0.2 $\mu$m, was obtained.

Comparative Example 2

The procedure was carried out in the same manner as in Example 1 except that 70 g of methyl methacrylate, and 10 g of ethyleneglycol dimethacrylate were used as the monomers for forming a surface layer. And the powder of fine particles having an average particle diameter of 10.2 $\mu$m, average core diameter of 8.9 $\mu$m, and average surface layer thickness of 0.65 $\mu$m, was obtained.

Comparative Example 3

The procedure was carried out in the same manner as in Example 1 without adding monomers for forming a surface layer. The resultant particles fused and coagulated into lumps through filtration and drying, and could not pulverized into the powder of spherical particles.

Example 4

The powders of fine particles produced in Examples 1 to 3, and in Comparative Examples 1 and 2, and the powder of spherical polymethyl methacrylate particles (PMMA powder, of which average particle diameter was 8 $\mu$m) were tested by a panel of subjects, ten women. The powder samples were placed and spread well on the back of their hands, and the touch on skin of the powders was evaluated.

The result is shown in Table 1.

The powders of fine particles of Examples 1 to 3 gave soft and smooth touch on skin, and evaluated to be superior. On the contrary, the powders of fine particles of Comparative Examples 1 and 2, and the PMMA powder were evaluated to be poor because of a little gritty and hard touch, though their particle size was not so different from that of the particles of Examples 1 to 3.

TABLE 1

| Powder | Result of Test | | |
| --- | --- | --- | --- |
| | Powder | in Cream | in Cosmetic powder |
| Example 1 | 4.8 | 5.0 | 4.6 |
| Example 2 | 4.6 | 4.8 | 4.6 |
| Example 3 | 4.6 | 4.8 | 4.8 |
| Comparative Example 1 | 2.8 | 3.2 | 2.8 |
| Comparative Example 2 | 3.0 | 3.5 | 3.4 |
| PMMA powder | 3.2 | 3.4 | 3.4 |

Testing: Test samples were placed on the back of the hands of 10 subjects, and rubbed with fingers well to evaluate their touch, softness, and smoothness according to the following standard, good 5, medium 3, and poor 1. The figures on Table 1 are the average of the evaluation.

Example 5

The creams were prepared by the formulation shown in Table 2 with the powders of fine particles synthesized in Examples 1 to 3, and in Comparative Examples 1 and 2, and the PMMA powder, and tested in the same manner as in Example 4. The result is shown in Table 1. The creams containing the powders of Examples 1 to 3 were evaluated to be superior. On the contrary, the creams containing the powders of Comparative Examples and the PMMA powder were evaluated to be poor.

TABLE 2

| Components | Weight percent |
| --- | --- |
| Powder of fine particles | 12.0 |
| Solid paraffin wax | 5.0 |
| Vaseline | 14.0 |
| Liquid paraffin | 40.0 |
| Glycerin monostealate | 2.0 |
| Polyoxyethylene sorbitan monooleate | 2.0 |
| Purified water | 23.7 |
| Powder soap | 0.1 |
| Borax | 0.2 |
| Perfumes | 1.0 |
| Antioxidants and antiseptics | proper quantity |

Example 6

The cosmetic powders were prepared by the formulation shown in Table 3 using the powders of fine particles synthesized in Examples 1 to 3, and in Comparative Examples 1 and 2, and the PMMA powder, and tested in the same manner as in Example 4. The result is shown in Table 1. The cosmetic powders containing the powders of Examples 1 to 3 gave soft and smooth touch on skin, and were evaluated to be superior. On the contrary, the cosmetic powders containing the powders of Comparative Examples and the PMMA powder were evaluated to be poor.

TABLE 3

| Components | Weight percent |
| --- | --- |
| Powder of fine particles | 80.0 |
| Zinc oxide | 5.0 |
| Zinc stearate | 5.0 |
| Rice starch | 10.0 |
| Perfume and colorants | proper quantity |

Example 7

An oil phase was prepared by mixing 30 g of the compound represented by the above-mentioned formula (1), 80 g of methyl methacrylate, 10 g of ethyleneglycol dimethacrylate, 30 g of toluene, and 1 g of azobisisobutylonitryl into a homogeneous solution. A water phase was prepared by dissolving 1.6 g of methyl cellulose 0.1 g of sodium dioctylsulfosuccinate, and 0.1 g of sodium hexamethaphosphate in 420 g of purified water.

Then the above-mentioned oil phase and water phase were mixed into homogeneous suspension through 2 minutes high-speed agitation with a T.K. Homomixer (produced by Tokushu Kika Kougyo K.K.). The suspension was then charged into a 1.5-liter autoclave. After replacing the inside atmosphere of the reaction system with $N_2$, polymerization was carried out at 65° C. for 7 hours with agitation at 200 rpm. After 7 hours, the reacted liquid was cooled down to normal temperature.

The average particle diameter of the core polymer particles obtained in the above reaction was 9.0 $\mu$m. Then 20 g of methyl methacrylate containing 0.15 g of azobisisobutylonitryl, and 2.5 g of ethyleneglycol dimethacrylate were added in the reaction liquid. The liquid was reacted with agitation at 200 rpm being reheated at 65° C. for 5 hours.

After the reaction, the liquid was cooled down to normal temperature, and the resultant particles were separated from the dispersion medium by filtration. The particles were washed with water and filtered two times. Then the washed particles were dried and pulverized into the powder of fine particles of the present invention. The particles of the powder had an average diameter of 9.4 $\mu$m, and had a surface layer of 0.2 $\mu$m average thickness formed on the surface of the cores of the particles.

One part by weight of the particles obtained in the reaction was dispersed in 999 parts by weight of each of ester oil silicone oil, and squalene, in which reactive benzotriazole compounds were soluble and polyacrylic resin was insoluble, by subjecting to ultrasonic radiation for 3 minutes. After standing the dispersion for 24 hours at 40° C., the supernatant liquid was fractionated, and the particles contained in the liquid were separated by centrifugal separation at 2000 rpm for 20 minutes. The absorbency of the remaining oil was measured and compared with the calibration curve of 2-(2'hydroxy-5'-methacryloxy ethylphenyl)-2H-benzotriazole to determine the quantity of the ultraviolet-ray absorber dissolved out in the oil. The quantity of the dissolved ultraviolet-ray absorber was represented by the ratio to the whole quantity of the ultraviolet-ray absorber (encapsulated in particles) contained in the particles added to the oils.

The result is given in Table 4.

Example 8

The powder of the fine particles, having an average particle diameter of 9.4 $\mu$m, average core diameter of 9.0 $\mu$m and average surface layer thickness of 0.2 $\mu$m, of the present invention was produced in the same manner as in Example 7 except that 25 g of the compound represented by the above-mentioned formula (1), 65 g of methyl methacrylate 20 g of ethyl methacrylate, 10 g of ethyleneglycol dimethacrylate, and 30 g of toluene were used as monomers for forming cores. The quantity of the ultraviolet-ray absorber dissolved out from the resultant fine particles was measured in the same procedure as in Example 7.

Example 9

The powder of the fine particles, having an average particle diameter of 8.5 $\mu$m, average core diameter of 8.2 $\mu$m and average surface layer thickness of 0.15 $\mu$m, of the present invention was produced in the same manner as in Example 7 except that 17.5 g of ethyl methacrylate and 5 g of ethyleneglycol dimethacrylate were used as monomers for forming a surface layer. The quantity of the ultraviolet-ray absorber dissolved out from the resultant particles was. measured in the same procedure as in Example 7.

Comparative Example 4

Fine particles, having an average particle diameter of 9.2 $\mu$m, average core diameter of 8.8 $\mu$m, and average surface layer thickness of 0.2 $\mu$m, were produced in the same manner as in Example 7 except that toluene was replaced by methyl methacrylate. The quantity of the ultraviolet-ray absorber dissolved out from the resultant particles was measured in the same manner as in Example 7.

Comparative Example 5

Fine particles having an average particle diameter of 8.5 $\mu$m, average core diameter of 8.2 $\mu$m, and average surface layer thickness of 0.15 μm were produced in the same manner as in Example 7 except that 2-(2'-hydroxy-5'-methacryloxy ethylphenyl)-2H-benzotriazole was replaced by 4-tert-butyl-4'-methoxydibenzoyl methane (ultraviolet-ray absorber).

One part by weight of the particles obtained was dispersed in 999 weight parts of each of ester oil silicone oil and squalane, in which reactive benzotriazol compounds were soluble and polyacrylate resin was insoluble, by subjecting to ultrasonic radiation for 3 minutes. After standing the dispersion for 24 hours at 40° C., the supernatant liquid was fractionated, and the particles contained in the liquid were separated by centrifugal separation at 2000 rpm for 20 minutes. The absorbency of the remaining oil was measured and compared with the calibration curve of 4-tert-butyl-4'-methoxydibenzoyl methane to determine the quantity of the ultraviolet-ray absorber dissolved out in the oil. The quantity of the dissolved ultraviolet-ray absorber was represented by the ratio to the whole quantity of the ultraviolet-ray absorber (encapsulated in particles) contained in the particles added to the oils.

The result is given in Table 4.

TABLE 4

| Test No. | Oils used to dissolve out the absorber | | |
|---|---|---|---|
| | ester | silicone | squalane |
| Particles of Example 7 | 70 ppm | 30 ppm | 30 ppm |
| Particles of Example 8 | 60 ppm | 20 ppm | 20 ppm |
| Particles of Example 9 | 60 ppm | 20 ppm | 20 ppm |
| Particles of Comparative Example 4 | 0.02% | 0.01% | 0.01% |
| Particles of Comparative Example 5 | 0.3% | 0.1% | 0.1% |

The ultraviolet-ray absorber dissolved out from the particles of Examples 7 to 9 shown in the above Table 4 may be unreacted 2-(2'-hydroxy-5'-methacryloxy ehtylphenyl)-2H-benzotriazole (represented by the formula (1)) sticked on the particles. Such dissolving of the agent can almost be prevented by washing particles.

Example 10

The particles produced in the above Examples 7 to 9 were blended in a foundation by 10 weight percent of the foundation, and evaluated for irritation test. Rough skin caused from ultraviolet-ray absorbers was not found, and the foundation samples had sufficient sunscreening performance.

What is claimed is:

1. Synthetic organic particles having an average particle size of 1.02 to 18 μm, and comprising:
   (A) cores of an organic polymer, the said organic polymer comprising a copolymer of 80 to 99 weight percent of lower alkyl acrylate and 1 to 20 weight percent of polyfunctional vinyl monomer, said copolymer having rubbery elasticity; and
   (B) a surface layer of a methacrylate resin being formed on the surface of the said cores; and having
   (C) rubbery elasticity.

2. The synthetic organic particles of claim 1, wherein the lower alkyl acrylate is an alkyl ester of acrylic acid, said alkyl having 1 to 4 carbon atoms.

3. The synthetic organic particles of claim 1, wherein the polyfunctional vinyl monomer contains at least two ethylenically unsaturated bonds in the molecule.

4. The synthetic organic particles of claim 1, wherein the methacrylate resin is a polymer of a lower alkyl methacrylate, or a copolymer of a lower alkyl methacrylate and a polyfunctional vinyl monomer.

5. The synthetic organic particles of claim 1, wherein the cores are spherical and have an average diameter of 1 to 16 μm.

6. The synthetic organic particles of claim 1, wherein the surface layer has an average thickness of 0.01 to 1 μm.

7. A process for producing synthetic organic particles comprising:
   (1) suspension polymerizing 80 to 99 weight percent of lower alkyl acrylate and 1 to 20 weight percent of polyfunctional vinyl monomer in an aqueous medium to form core particles of an organic polymer having rubbery elasticity; and
   (2) adding lower alkyl methacrylate or a combination of lower alkyl methacrylate and polyfunctional vinyl monomer in the polymerization system containing the said core particles, and polymerizing the added monomer(s) on the surface of the said core particles to form a surface layer of methacrylate resin on the surface of the said core particles.

8. Synthetic organic particles having an average particle size of 1.02 to 18 μm, and comprising:
   (A') cores of organic polymer, said polymer being a copolymer of a reactive benzotriazol compound and (meth)acrylic monomer, and having ultraviolet-ray absorbing function; and
   (B') a surface layer of a methacrylate resin and formed on the surface of said cores; said particles having
   (C') ultraviolet-ray absorbing function.

9. The synthetic organic particles of claim 8, wherein the reactive benzotriazol compound is represented by the following formula (1)

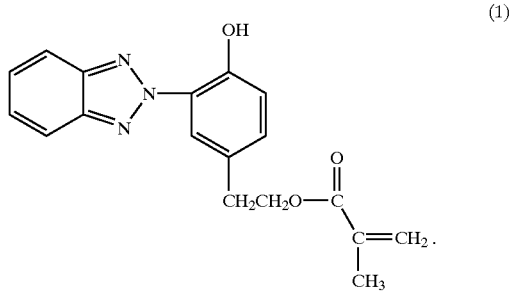

10. The synthetic organic particles of claim 8, wherein the (meth)acrylate monomer is selected from the group consisting of methyl (meth)acrylate, ethyl (meth)acrylate, propyl (meth)acrylate, butyl (meth)acrylate, 2-ethylhexyl (meth)acrylate, lauryl (meth)acrylate, stearyl (meth)acrylate, cyclohexyl (meth)acrylate, 2-hydroxyethyl (meth)acrylate, 2-propyl (meth)acrylate, chloro-2-hydroxyethyl (meth)acrylate, diethylene glycol mono(meth)acrylate, methoxy ethyl (meth)acrylate, glycidyl (meth)acrylate, dicyclopentanyl (meth)acrylate, dicyclopentanyl (meth)acrylate and isobornyl (meth)acrylate.

11. The synthetic organic particles of claim 8, wherein the copolymer of the organic polymer is further copolymerized with a polyfunctional monomer.

12. The synthetic organic particles of claim 8, wherein the methacrylate resin is a polymer of lower alkyl methacrylate, or a copolymer of lower alkylmethacrylate and polyfunctional vinyl monomer.

13. The synthetic organic particles of claim 8, wherein the cores are spherical and have an average diameter of 1 to 16 µm.

14. The synthetic organic particles of claim 8, wherein the surface layer has an average thickness of 0.01 to 1 µm.

15. A process for producing synthetic organic particles comprising:
   (1) dispersing a reactive benzotriazol compound, (meth) acrylic monomer and toluene in an aqueous medium, and polymerizing them to form polymer particles, in which toluene is encapsulated,
   (2) adding lower alkyl methacrylate or a combination of lower alkyl methacrylate and polyfunctional vinyl monomer in the polymerization system containing the said polymer particles and polymerizing the added monomers on the surface of the said polymer particles to form a surface layer of methacrylate resin on the said polymer particles, and
   (3) separating the polymer particles having the surface layer produced in step (2) and drying the particles to evaporate and remove the encapsulated toluene from the polymer particles.

16. The process of claim 15 wherein the polymerization in the step (1) is carried out by-emulsion polymerization, soap-free emulsion polymerization, suspension polymerization or seed polymerization.

17. Synthetic organic particles according to claim 1, said particles having an average particle size of 3.1 to 14 µm.

18. Synthetic organic particles according to claim 17, wherein said cores have an average particle size of from 3 to 13 µm.

19. Synthetic organic particles according to claim 1, wherein said copolymer comprises from 3 to 15 weight percent of said polyfunctional vinyl monomer.

20. Synthetic organic particles according to claim 1, wherein said polyfunctional vinyl monomer comprises (poly)ethyleneglycol di(meth)acrylate or trimethylolpropane tri(meth)acrylate.

21. Synthetic organic particles according to claim 8, said particles having an average particle size of 3.1 to 14 µm.

22. Synthetic organic particles according to claim 21, wherein said cores have an average particle size of from 3 to 13 µm.

23. Synthetic organic particles according to claim 8, wherein said copolymer comprises from 1 to 40 parts by weight of said reactive benzotriazol compound per 100 parts by weight of (meth)acrylic monomer.

24. Synthetic organic particles according to claim 8, wherein said copolymer comprises from 10 to 30 parts by weight of said reactive benzotriazol compound per 100 parts by weight of (meth)acrylic monomer.

25. A cosmetic composition comprising a cosmetic base and synthetic organic particles as set forth in claim 1.

26. The cosmetic composition according to claim 25, wherein said cosmetic base is a cosmetic cream base.

27. The cosmetic composition according to claim 25, wherein said cosmetic base is a cosmetic powder base.

28. A cosmetic composition comprising a cosmetic base and synthetic organic particles as set forth in claim 8.

29. A process for producing synthetic organic particles comprising:
   (1) polymerizing 80 to 99 weight percent of lower alkyl acrylate and 1 to 20 weight percent of polyfunctional vinyl monomer in an aqueous medium to form core particles of organic polymer having rubbery elasticity, said core particles having an average particle diameter of from 1 to 16 µm; and
   (2) adding lower alkyl methacrylate or a combination of lower alkyl methacrylate and polyfunctional vinyl monomer in the polymerization system containing said core particles, and polymerizing the added monomer(s) on the surface of said core particles to form a surface layer of methacrylate resin on the surface of said core particles, and wherein the average size of the resulting particles comprising the core particles and surface layer is from 1.02 to 18 µm.

\* \* \* \* \*